(12) United States Patent
Lindquist et al.

(10) Patent No.: US 9,738,898 B2
(45) Date of Patent: Aug. 22, 2017

(54) YEAST CELLS EXPRESSING TAR DNA-BINDING PROTEIN 43 AND USES THEREFOR

(75) Inventors: Susan L. Lindquist, Chestnut Hill, MA (US); Aaron D. Gitler, Philadelphia, PA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 1345 days.

(21) Appl. No.: 12/867,724

(22) PCT Filed: Feb. 13, 2009

(86) PCT No.: PCT/US2009/034117
§ 371 (c)(1),
(2), (4) Date: Nov. 1, 2010

(87) PCT Pub. No.: WO2009/102995
PCT Pub. Date: Aug. 20, 2009

(65) Prior Publication Data
US 2011/0053857 A1 Mar. 3, 2011

Related U.S. Application Data

(60) Provisional application No. 61/029,168, filed on Feb. 15, 2008.

(51) Int. Cl.
*G01N 33/53* (2006.01)
*C12N 15/81* (2006.01)
*C12N 15/10* (2006.01)
*G01N 33/68* (2006.01)

(52) U.S. Cl.
CPC ......... *C12N 15/81* (2013.01); *C12N 15/1079* (2013.01); *G01N 33/6872* (2013.01); *G01N 33/6896* (2013.01); *G01N 2500/10* (2013.01)

(58) Field of Classification Search
CPC ........... C07K 16/18; G01N 2800/2821; G01N 2800/52; G01N 33/6896
USPC ........................................ 435/7.1; 530/387.1
See application file for complete search history.

(56) References Cited

U.S. PATENT DOCUMENTS

| | | | |
|---|---|---|---|
| 7,045,290 | B2 | 5/2006 | Lindquist et al. |
| 7,452,670 | B2 | 11/2008 | Muchowski et al. |
| 7,799,535 | B1 | 9/2010 | Lindquist |
| 8,039,209 | B2 | 10/2011 | Lindquist et al. |
| 8,133,679 | B2 | 3/2012 | Muchowski et al. |
| 8,192,986 | B2 | 6/2012 | Lindquist et al. |
| 8,399,241 | B2 | 3/2013 | Lindquist et al. |
| 2004/0048237 | A1 | 3/2004 | Lindquist et al. |
| 2006/0147902 | A1* | 7/2006 | Lindquist et al. ............... 435/4 |
| 2009/0263824 | A1* | 10/2009 | Lee et al. ....................... 435/7.1 |
| 2013/0045483 | A1 | 2/2013 | Treusch et al. |

FOREIGN PATENT DOCUMENTS

| | | |
|---|---|---|
| WO | WO 99/29891 | 6/1999 |
| WO | WO 2004/093790 | 11/2004 |
| WO | WO 2005/107792 | 11/2005 |
| WO | WO 2006/124892 | 11/2006 |
| WO | WO 2009/086306 | 7/2009 |
| WO | WO 2011/088059 | 7/2011 |

OTHER PUBLICATIONS

Buratti and Baralle, "Characterization and functional implications of the RNA binding properties of nuclear factor TDP-43, a novel splicing regulator of CFTR exon 9," *J. Biol. Chem.*, 2001, 276(39):36337-43.
Cairns et al., "TDP-43 in familial and sporadic frontotemporal lobar degeneration with ubiquitin inclusions," *Am. J. Pathol.*, 2007, 171(1):227-40.
Dickson, "TDP-43 immunoreactivity in neurodegenerative disease: disease versus mechanism-specificity," *Acta. Neuropathol.*, 2008,115(1):147-149.
Forman et al., "TDP-43: a novel neurodegenerative proteinopathy," *Current Opinion in Neurobiology*, 2007, 17:548-555.
International Search Report and Written Opinion in International Application No. PCT/US2009/034117, mailed Jul. 13, 2009, 18 pages.
International Preliminary Report on Patentability in International Application No. PCT/US2009/034117, mailed Aug. 26, 2010, 8 pages.
Johnson et al., "A yeast TDP-43 proteinopathy model: exploring the molecular determinants of TDP-43 aggregation and cellular toxicity," *PNAS*, Apr. 2008, 105(17):6439-6444.
Mackenzie et al., "Pathological TDP-43 distinguishes sporadic amyotrophic lateral sclerosis from amyotrophic lateral sclerosis with SOD1 mutations," *Ann Neurol*, 2007, 61:427-434.
Neumann et al., "Ubiquitinated TDP-43 in frontotemporal lobar degeneration and amyotrophic latertal sclerosis," *Science*, Oct. 2006, 314:130-133.
Ou et al., "Cloning and characterization of a novel cellular protein, TDP-43, that binds to human immunodeficiency virus type 1 TAR DNA sequence motifs," *J. Virology*, 1995, 69(6):3584-3596.
Rothstein, TDP-43 in amyotrophic lateral sclerosis: Pathophysiology or patho-babel? *Ann Neurol*, 2007, 61:382-384.
Sampathu et al., Pathological heterogeneity of frontotemporal lobar degeneration with ubiquitin-positive inclusions delineated by ubiquitin immunohistochemistry and novel monoclonal antibodies. *Am J Pathol*, 2006, 169:1343-1352.

* cited by examiner

*Primary Examiner* — Nancy Treptow
(74) *Attorney, Agent, or Firm* — Fish & Richardson P.C.

(57) ABSTRACT

Disclosed are yeast cells expressing TAR DNA-binding protein 43 (TDP-43) and methods of screening yeast cells to identify compounds that prevent or suppress TDP-43-induced toxicity, compounds that inhibit the formation or maintenance of cytoplasmic inclusions of TDP-43, genetic suppressors or enhancers of TDP-43-induced toxicity, and genetic suppressors or enhancers of the formation or maintenance of cytoplasmic inclusions of TDP-43. Compounds identified by such screens can be used to treat or prevent TDP-43 proteinopathies such as frontotemporal lobar degeneration or amyotrophic lateral sclerosis.

26 Claims, 1 Drawing Sheet

US 9,738,898 B2

YEAST CELLS EXPRESSING TAR DNA-BINDING PROTEIN 43 AND USES THEREFOR

CROSS REFERENCE TO RELATED APPLICATIONS

This application is a national phase filing under 35 U.S.C. 371 of international application number PCT/US2009/034117, filed Feb. 13, 2009, which claims priority from U.S. Provisional Application No. 61/029,168, filed Feb. 15, 2008. The entire content of each of these prior applications is incorporated herein by reference in its entirety.

STATEMENT AS TO FEDERALLY SPONSORED RESEARCH

This invention was made with Government support under grant number 2P50 NS038372-0681. The Government has certain rights in the invention.

TECHNICAL FIELD

The invention relates to protein chemistry and cellular and molecular biology

BACKGROUND

TDP-43 (TAR DNA-Binding Protein 43) was identified as a protein that binds to human immunodeficiency virus type 1 TAR DNA sequence motifs and represses transcription of viral RNA (Ou, S., *J Virol.*, 69(6):3584-96, 1995). TDP-43 was also identified as a splicing regulator that binds to the (UG)m-repeated polymorphic region near the 3' splice site of CFTR exon 9 and down-regulates its recognition by the splicing machinery (Buratti, E. and Baralle F E, *J Biol Chem.*, 276(39):36337-43, 2001 and references therein). Notably, exon 9 skipping produces a nonfunctional CFTR protein and is associated with some forms of cystic fibrosis. It was also observed that TDP-43 recognizes (UG) repeats in other contexts.

Hyperphosphorylated, ubiquitinated, C-terminal fragments of TDP-43 have been recovered from the central nervous system (e.g., hippocampus, neocortex, and spinal cord) from patients with frontotemporal lobar degeneration (FTLD) with ubiquitin-positive inclusions and amyotrophic lateral sclerosis (ALS) and is believed to be the hallmark pathological feature of FTLD and ALS (Neumann et al. *Science*, 314(5796):130-3. 2006). The presence or amount of abnormal aggregation of phosphorylated and ubiquitinated TDP-43 is believed to define a novel class of neurodegenerative diseases referred to as "TDP-43 proteinopathies" (Cairns et al. (2007) The American Journal of Pathology 171(1):227).

SUMMARY

The invention is based, at least in part, on the discovery that expression of a human TDP-43 protein in yeast cells is toxic and results in the formation of TDP-43-containing insoluble cytoplasmic inclusions. This discovery permits the carrying out of screens using TDP-43-expressing yeast cells to identify compounds or genetic factors that modulate TDP-43-induced toxicity or TDP-43-induced inclusion formation. Compounds identified by such screens can be used for the treatment or prevention of TDP-43 proteinopathies such as frontotemporal lobar degeneration or amyotrophic lateral sclerosis.

Described herein is a yeast cell containing an expression construct containing a promoter operably linked to a nucleic acid encoding a polypeptide containing a TAR DNA-binding protein 43 (TDP-43) protein, wherein expression of the nucleic acid and production of the polypeptide results in a decrease in growth or viability of the cell. In some embodiments, expression of the nucleic acid and production of the polypeptide renders the yeast cell non-viable.

The expression construct can optionally be integrated in the genome of the yeast cell. For example, the expression construct can be an integrative plasmid such as pRS303, pRS304, pRS305, or pRS306. A yeast cell can have one or more (e.g., two, three, or four) integrated copies of an expression construct.

The promoter can be an inducible promoter such as GAL1-10, GAL1, GALL, GALS, GPD, ADH, TEF, CYC1, MRP7, MET25, TET, VP16, or VP16-ER. Alternatively, the promoter can be a constitutively active promoter.

In some embodiments, the TDP-43 protein is human TDP-43. The polypeptide can optionally contain a full length TDP-43 protein (e.g., SEQ ID NO:1). The polypeptide can be a fusion protein containing a detectable protein (e.g., a fluorescent protein, an enzyme, or an epitope). Exemplary fluorescent proteins include red fluorescent protein, green fluorescent protein, blue fluorescent protein, yellow fluorescent protein, and cyan fluorescent protein.

In some embodiments, the yeast is *Saccharomyces cerevisiae*, *Saccharomyces uvae*, *Saccharomyces kluyveri*, *Schizosaccharomyces pombe*, *Kluyveromyces lactis*, *Hansenula polymorpha*, *Pichia pastoris*, *Pichia methanolica*, *Pichia kluyveri*, *Yarrowia lipolytica*, *Candida* sp., *Candida utilis*, *Candida cacaoi*, *Geotrichum* sp., or *Geotrichum fermentans*.

In some embodiments, at least one gene that encodes a protein involved in drug efflux or cell permeability is disrupted in the yeast cell. For example, one or more of the genes PDR1, PDR3, PDR5, SNQ2, or ERG6 can be disrupted in the yeast cell.

Also disclosed is a method of inducing toxicity in a yeast cell by: providing a yeast cell described herein; and inducing a level of expression of the nucleic acid in the yeast cell that is toxic to the yeast cell.

Also disclosed is a method of identifying a compound that prevents or suppresses TDP-43-induced toxicity by: culturing a yeast cell described herein in the presence of a candidate agent and under conditions that allow for expression of the nucleic acid at a level that, in the absence of the candidate agent, is sufficient to induce toxicity in the cell; measuring cell growth or viability in the presence of the candidate agent; and comparing cell growth or viability measured in the presence of the candidate agent to cell growth or viability in the absence of the candidate agent, wherein if cell growth or viability is increased in the presence of the candidate agent as compared to in the absence of the candidate agent, then the candidate agent is identified as a compound that prevents or suppresses TDP-43-induced toxicity.

Also disclosed is a method of identifying a compound that inhibits the formation or maintenance of cytoplasmic inclusions of TDP-43 by: providing a yeast cell containing an expression construct containing a nucleic acid encoding a protein containing TDP-43; culturing the yeast cell in the presence of a candidate agent and under conditions that allow for expression of the nucleic acid at a level that, in the absence of the candidate agent, is sufficient to result in the formation or maintenance of cytoplasmic inclusions of the protein; measuring the formation or maintenance of cytoplasmic inclusions of the protein in the presence of the candidate agent; and comparing the formation or maintenance of cytoplasmic inclusions of the protein measured in the presence of the candidate agent to the formation or maintenance of cytoplasmic inclusions of the protein in the absence of the candidate agent, wherein if formation or maintenance of cytoplasmic inclusions of the protein is decreased in the presence of the candidate agent as compared to in the absence of the candidate agent, then the candidate agent is identified as a compound that inhibits the formation or maintenance of cytoplasmic inclusions of TDP-43.

Also disclosed is a method of identifying a genetic suppressor or enhancer of TDP-43-induced toxicity by: providing a yeast cell described herein, wherein the yeast cell has been genetically modified to overexpress a gene; culturing the yeast cell under conditions that allow for expression of the protein at a level that, in the absence of overexpression of the gene, is sufficient to induce toxicity in the yeast cell; measuring cell growth or viability in the presence of overexpression of the gene; and comparing cell growth or viability measured in the presence of overexpression of the gene to cell growth or viability in the absence of overexpression of the gene, wherein (i) if cell growth or viability is increased in the presence of overexpression of the gene as compared to in the absence overexpression of the gene, then the gene is identified as a genetic suppressor of TDP-43-induced toxicity, and (ii) if cell growth or viability is decreased in the presence of overexpression of the gene as compared to in the absence overexpression of the gene, then the gene is identified as a genetic enhancer of TDP-43-induced toxicity.

Also disclosed is a method of identifying a genetic suppressor or enhancer of TDP-43-induced toxicity by: providing a yeast cell described herein, wherein an endogenous gene of the yeast cell has been disrupted; culturing the yeast cell under conditions that allow for expression of the protein at a level that, in the absence of disruption of the endogenous gene, is sufficient to induce toxicity in the yeast cell; measuring cell growth or viability in the presence of disruption of the endogenous gene; and comparing cell growth or viability measured in the presence of disruption of the endogenous gene to cell growth or viability in the absence of disruption of the endogenous gene, wherein (i) if cell growth or viability is increased in the presence of disruption of the endogenous gene as compared to in the absence disruption of the endogenous gene, then the gene is identified as a genetic enhancer of TDP-43-induced toxicity, and (ii) if cell growth or viability is decreased in the presence of disruption of the endogenous gene as compared to in the absence disruption of the endogenous gene, then the gene is identified as a genetic suppressor of TDP-43-induced toxicity.

Also disclosed is a method of treating a TDP-43 proteinopathy by administering to a subject (e.g., a human) having, or at risk of developing, a TDP-43 proteinopathy a pharmaceutical composition containing a therapeutically effective amount of a compound identified by a method described herein.

In some embodiments, the TDP-43 proteinopathy is a frontotemporal dementia such as frontotemporal lobar degeneration. For example, the frontotemporal dementia can be frontotemporal lobar degeneration with tau-positive inclusions or frontotemporal lobar degeneration with ubiquitin-positive, tau- and alpha-synuclein negative inclusions. Frontotemporal lobar degeneration with tau-positive inclusions include frontotemporal lobar degeneration with Pick bodies, corticobasal degeneration, progressive supranuclear palsy, and neurofibrillary tangle-only dementia.

In some embodiments, the TDP-43 proteinopathy is amyotrophic lateral sclerosis.

Also disclosed is a method of reducing the amount, or preventing the occurrence, of aggregate TDP-43 in a cell (e.g., a human cell) by contacting a cell containing aggregate TDP-43 with a compound identified by a method described herein.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present application, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
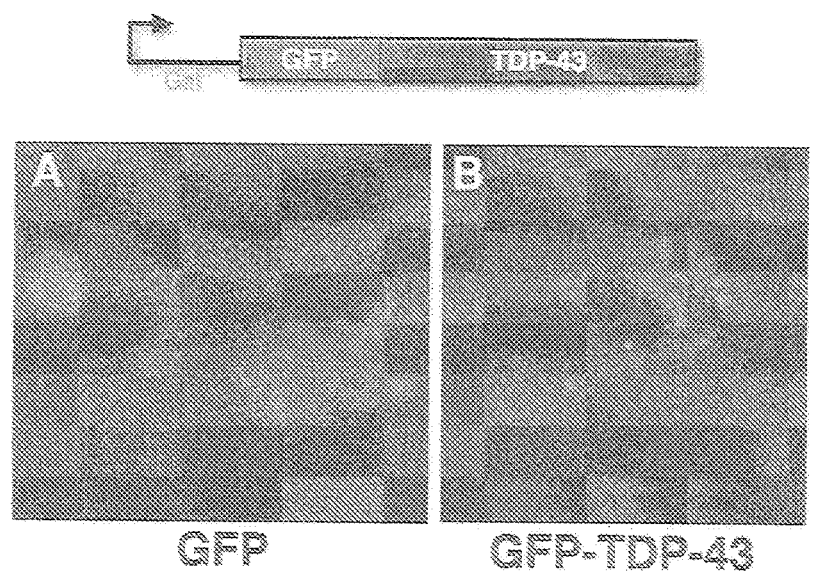
FIG. 1 is a photograph of yeast cells expressing GFP alone (A) or GFP fused to full length human TDP-43 (B). Induction of GFP-TDP-43 expression resulted in the formation of multiple cytoplasmic inclusions in the yeast cells.

The TDP-43-expressing yeast cells described herein can be used to identify compounds or genetic factors that modulate TDP-43-induced toxicity and/or TDP-43-induced inclusion formation. Compounds identified by such screens can be used for the treatment or prevention of neurodegenerative diseases characterized by abnormal aggregation of TDP-43. For example, compounds that inhibit or reverse aggregation of TDP-43 would be expected to be of use as therapeutic agents in neurodegenerative diseases in which TDP-43 aggregation plays a role.

TDP-43 Proteins and Nucleic Acids

Described herein are compositions and methods for identifying candidate compounds that prevent or suppress TDP-43-induced toxicity, candidate compounds that inhibit the formation or maintenance of cytoplasmic inclusions of TDP-43, genetic suppressors or enhancers of TDP-43-induced toxicity, and genetic suppressors or enhancers of the formation or maintenance of cytoplasmic inclusions of TDP-43.

A TDP-43 protein used in the compositions and methods described herein contains the sequence of a naturally occurring TDP-43 polypeptide or a biologically active fragment or variant thereof. A "biologically active" fragment or variant of a naturally occurring TDP-43 polypeptide retains the ability to induce a decrease cell growth or viability and/or induce formation of cytoplasmic inclusions in a yeast cell in which the fragment or variant is expressed. A biologically active fragment or variant of a TDP-43 polypeptide can contain one or more additions, substitutions, and/or deletions relative to the sequence of a naturally occurring TDP-43 polypeptide.

Human TDP-43 is 414 amino acids in length and has the following amino acid sequence (GenBank™ Reference NP_031401):

(SEQ ID NO: 1)
MSEYIRVTEDENDEPIEIPSEDDGTVLLSTVTAQFPGACGLRYRNPVS

QCMRGVRLVEGILHAPDAGWGNLVYVVNYPKDNKRKMDETDASSAVKV

KRAVQKTSDLIVLGLPWKTTEQDLKEYFSTFGEVLMVQVKKDLKTGHS

KGFGFVRFTEYETQVKVMSQRHMIDGRWCDCKLPNSKQSQDEPLRSRK

VFVGRCTEDMTEDELREFFSQYGDVMDVFIPKPFRAFAFVTFADDQIA

QSLCGEDLIIKGISVHISNAEPKHNSNRQLERSGRFGGNPGGFGNQGG

FGNSRGGGAGLGNNQGSNMGGGMNFGAFSINPAMMAAAQAALQSSWGM

MGMLASQQNQSGPSGNNQNQGNMQREPNQAFGSGNNSYSGSNSGAAIG

WGSASNAGSGSGFNGGFGSSMDSKSSGWGM.

C-terminal fragments of human TDP-43 have been recovered from the central nervous system of patients with frontotemporal lobar degeneration with ubiquitin-positive inclusions and amyotrophic lateral sclerosis (Neumann et al. *Science,* 314(5796):130-3. 2006). The disease associated C-terminal fragments of TDP-43 correspond to approximately amino acid residues 252-414 of SEQ ID NO:1.

In some embodiments, a variant TDP-43 polypeptide (i) contains one or more amino acid substitutions, and (ii) is at least 70%, 80%, 85%, 90%, 95%, 98% or 99% identical to SEQ ID NO:1 (or 70%, 80%, 85%, 90%, 95%, 98% or 99% identical to amino acids 252-414 of SEQ ID NO:1). A variant TDP-43 polypeptide differing in sequence from SEQ ID NO:1 (or differing in sequence from amino acids 252-414 of SEQ ID NO:1) may include one or more amino acid substitutions (conservative or non-conservative), one or more deletions, and/or one or more insertions. In an exemplary embodiment, a biologically active TDP-43 fragment contains amino acid residues 252-414 of SEQ ID NO:1.

Nucleic acids encoding variant TDP-43 polypeptides can be used to identify those variants that exhibit enhanced toxicity in yeast cells relative to that exhibited by the human TDP-43 protein of SEQ ID NO:1. Such enhanced toxicity variants are of use in the screening and other methods described herein.

A fusion protein containing a TDP-43 protein may be used. For example, a TDP-43 protein may be fused with a second domain. The second domain of the fusion protein can optionally be an immunoglobulin element, a dimerizing domain, a targeting domain, a stabilizing domain, or a purification domain. Alternatively, a TDP-43 protein can be fused with a heterologous molecule such as a detection protein. Exemplary detection proteins include: a fluorescent protein such as green fluorescent protein (GFP), cyan fluorescent protein (CFP) or yellow fluorescent protein (YFP); an enzyme such as β-galactosidase or alkaline phosphatase (AP); and an epitope such as glutathione-S-transferase (GST) or hemagglutinin (HA). To illustrate, a TDP-43 protein can be fused to GFP at the N- or C-terminus or other parts of the TDP-43 protein. These fusion proteins provide methods for rapid and easy detection and identification of the TDP-43 protein in the recombinant yeast cell.

Human TDP-43 is encoded by the following nucleotide sequence (GenBank™ Reference NM_007375):

(SEQ ID NO: 2)
GGTGGGCGGGGGAGGAGGCGGCCCTAGCGCCATTTTGTGGGAGCGAA

GCGGTGGCTGGGCTGCGCTTGGGTCCGTCGCTGCTTCGGTGTCCCTGT

CGGGCTTCCCAGCAGCGGCCTAGCGGGAAAAGTAAAAGATGTCTGAAT

ATATTCGGGTAACCGAAGATGAGAACGATGAGCCCATTGAAATACCAT

CGGAAGACGATGGGACGGTGCTGCTCTCCACGGTTACAGCCCAGTTTC

CAGGGGCGTGTGGGCTTCGCTACAGGAATCCAGTGTCTCAGTGTATGA

GAGGTGTCCGGCTGGTAGAAGGAATTCTGCATGCCCCAGATGCTGGCT

GGGGAAATCTGGTGTATGTTGTCAACTATCCAAAAGATAACAAAAGAA

AAATGGATGAGACAGATGCTTCATCAGCAGTGAAAGTGAAAAGAGCAG

TCCAGAAAACATCCGATTTAATAGTGTTGGGTCTCCCATGGAAAACAA

CCGAACAGGACCTGAAAGAGTATTTTAGTACCTTTGGAGAAGTTCTTA

TGGTGCAGGTCAAGAAAGATCTTAAGACTGGTCATTCAAAGGGGTTTG

GCTTTGTTCGTTTTACGGAATATGAAACACAAGTGAAAGTAATGTCAC

AGCGACATATGATAGATGGACGATGGTGTGACTGCAAACTTCCTAATT

CTAAGCAAAGCCAAGATGAGCCTTTGAGAAGCAGAAAAGTGTTTGTGG

GGCGCTGTACAGAGGACATGACTGAGGATGAGCTGCGGGAGTTCTTCT

CTCAGTACGGGGATGTGATGGATGTCTTCATCCCCAAGCCATTCAGGG

CCTTTGCCTTTGTTACATTTGCAGATGATCAGATTGCGCAGTCTCTTT

GTGGAGAGGACTTGATCATTAAAGGAATCAGCGTTCATATATCCAATG

CCGAACCTAAGCACAATAGCAATAGACAGTTAGAAAGAAGTGGAAGAT

TTGGTGGTAATCCAGGTGGCTTTGGGAATCAGGGTGGATTTGGTAATA

GCAGAGGGGTGGAGCTGGTTTGGGAAACAATCAAGGTAGTAATATGG

GTGGTGGGATGAACTTTGGTGCGTTCAGCATTAATCCAGCCATGATGG

CTGCCGCCCAGGCAGCACTACAGAGCAGTTGGGGTATGATGGGCATGT

TAGCCAGCCAGCAGAACCAGTCAGGCCCATCGGGTAATAACCAAAACC

AAGGCAACATGCAGAGGGAGCCAAACCAGGCCTTCGGTTCTGGAAATA

ACTCTTATAGTGGCTCTAATTCTGGTGCAGCAATTGGTTGGGGATCAG

CATCCAATGCAGGGTCGGGCAGTGGTTTTAATGGAGGCTTTGGCTCAA

GCATGGATTCTAAGTCTTCTGGCTGGGGAATGTAGACAGTGGGGTTGT

GGTTGGTTGGTATAGAATGGTGGGAATTCAAATTTTTCTAAACTCATG

GTAAGTATATTGTAAAATACATATGTACTAAGAATTTTCAAAATTGGT

TTGTTCAGTGTGGAGTATATTCAGCAGTATTTTTGACATTTTTCTTTA

GAAAAAGGAAGAGCTAAAGGAATTTTATAAGTTTTGTTACATGAAAGG

TTGAAATATTGAGTGGTTGAAAGTGAACTGCTGTTTGCCTGATTGGTA

AACCAACACACTACAATTGATATCAAAAGGTTTCTCCTGTAATATTTT

ATCCCTGGACTTGTCAAGTGAATTCTTTGCATGTTCAAAACGGAAACC

ATTGATTAGAACTACATTCTTTACCCCTTGTTTTAATTTGAACCCCAC

```
CATATGGATTTTTTCCTTAAGAAAATCTCCTTTTAGGAGATCATGGT
GTCACAGTGTTTGGTTCTTTTGTTTTGTTTTTTAACACTTGTCTCCCC
TCATACACAAAAGTACAATATGAAGCCTTCATTTAATCTCTGCAGTTC
ATCTCATTTCAAATGTTTATGGAAGAAGCACTTCATTGAAAGTAGTGC
TGTAAATATTCTGCCATAGGAATACTGTCTACATGCTTTCTCATTCAA
GAATTCGTCATCACGCATCACAGGCCGCGTCTTTGACGGTGGGTGTCC
CATTTTTATCCGCTACTCTTTATTTCATGGAGTCGTATCAACGCTATG
AACGCAAGGCTGTGATATGGAACCAGAAGGCTGTCTGAACTTTTGAAA
CCTTGTGTGGGATTGATGGTGGTGCCGAGGCATGAAAGGCTAGTATGA
GCGAGAAAAGGAGAGAGCGCGTGCAGAGACTTGGTGGTGCATAATGGA
TATTTTTTAACTTGGCGAGATGTGTCTCTCAATCCTGTGGCTTTGGTG
AGAGAGTGTGCAGAGAGCAATGATAGCAAATAATGTACGAATGTTTTT
TGCATTCAAAGGACATCCACATCTGTTGGAAGACTTTTAAGTGAGTTT
TTGTTCTTAGATAACCCACATTAGATGAATGTGTTAAGTGAAATGATA
CTTGTACTCCCCCTACCCCTTTGTCAACTGCTGTGAATGCTGTATGGT
GTGTGTTCTCTTCTGTTACTGATATGTAAGTGTGGCAATGTGAACTGA
AGCTGATGGGCTGAGAACATGGACTGAGCTTGTGGTGTGCTTTGCAGG
AGGACTTGAAGCAGAGTTCACCAGTGAGCTCAGGTGTCTCAAAGAAGG
GTGGAAGTTCTAATGTCTGTTAGCTACCCATAAGAATGCTGTTTGCTG
CAGTTCTGTGTCCTGTGCTTGGATGCTTTTTATAAGAGTTGTCATTGT
TGGAAATTCTTAAATAAAACTGATTTAAATAATATGTGTCTTTGTTTT
GCAGCCCTGAATGCAAAGAATTCATAGCAGTTAATTCCCCTTTTTTGA
CCCTTTTGAGATGGAACTTTCATAAAGTTTCTTGGCAGTAGTTTATTT
TGCTTCAAATAAACTTATTTGAAAAGTTGTCTCAAGTCAAATGGATTC
ATCACCTGTCATGCATTGACACCTGATACCCAGACTTAATTGGTATTT
GTTCTTGCATTGGCCAAAGTGAAAATTTTTTTTTTCTTTTGAAATCT
AGTTTTGAATAAGTCTGGGTGACCGCACCTAAAATGGTAAGCAGTACC
CTCCGGCTTTTTCTTAGTGCCTCTGTGCATTTGGGTGATGTTCTATTT
ACATGGCCTGTGTAAATCTCCATTGGGAAGTCATGCCTTCTAAAAGA
TTCTTATTTGGGGGAGTGGGCAAAATGTTGATTATTTTCTAATGCTTT
GTAGCAAAGCATATCAATTGAAAAGGGAATATCAGCACCTTCCTAGTT
TGGGATTTGAAAAGTGGAATTAATTGCAGTAGGGATAAAGTAGAAGAA
ACCACAAATTATCTTGTGCCTGAAATCCATTAAGAGGCCTGATAGCTT
TAAGAATTAGGGTGGGTTGTCTGTCTGGAAGTGTTAAGTGGAATGGGC
TTTGTCCTCCAGGAGGTGGGGAATGTGGTAACATTGAATACAGTTGA
ATAAAATCGCTTACAAAACTCACACTCTCACAATGCATTGTTAAGTAT
GTAAAGCAATAACATTGATTCTCTGTTGTACTTTTTTGTAACTAATT
CTGTGAGAGTTGAGCTCATTTTCTAGTTGGAAGAATGTGATATTTGTT
GTGTTGGTAGTTTACCTAATGCCCTTACCTAATTAGATTATGATAAAT
AGGTTTGTCATTTTGCAAGTTACATAAACATTTATCAATGAAGTCATC
CTTTAGACTTGTAATCGCCACATTGTTTCATTATTCAGTTTCCTCTGT
AAAGGGATCTTGAGTTGTTTTAATTTTTTTTTCTGCATCTGAATCTG
CATGATTTCCAAACCCTGTACCATCTGAATTTTGCATTTTAGCACTTG
CACTATTACTCAGCAGCAGTAACATGGTAACACTTAAAATGGTACTCG
GGGACCTCCAAAGACTAAACTGACAAGCCTTCAAGGAGCCCAGGGGTA
AGTTAACTTGTCAACGGCATGGTTTAATCCCTTCTTTACACTTGTGTA
AATTTCAGTTACTGGTCATAGAAGGCTTTCAATGTTGAGTGGCCTTTT
ATTAACATGTTTATGGTACTGCATAGATACGGGTATTTATTTTACCCT
AAGAAGATTTTGAAGTTTAAAAGTACTTAAACTATTTGGCAAAGATTT
GTTTTTAAAAATCTATTTGGTCAATCTAAATGCATTCATTCTAAAAAA
TTTTTTGAACCAGATAAATAAAATTTTTTTTTGACACCACAAAAAAAA
AAAAAAAAAAAA.
```
The coding region extends from nucleotides 135-1379 of SEQ ID NO: 2.

Also described herein are methods of preparing and transferring nucleic acids encoding a TDP-43 protein into a cell so that the cell expresses the TDP-43 protein. The term "TDP-43 nucleic acid" encompasses a nucleic acid containing a sequence as represented in SEQ ID NO:2 as well as a nucleic acid encoding any of the biologically active fragments or variants of TDP-43 described herein. Exemplary TDP-43 nucleic acids include those encoding full length human TDP-43 and C-terminal fragments thereof.

The term "nucleic acid" generally refers to at least one molecule or strand of DNA, RNA or a derivative or mimic thereof, containing at least one nucleobase, for example, a naturally occurring purine or pyrimidine base found in DNA or RNA. Generally, the term "nucleic acid" refers to at least one single-stranded molecule, but in specific embodiments will also encompass at least one additional strand that is partially, substantially or fully complementary to the at least one single-stranded molecule. Thus, a nucleic acid may encompass at least one double-stranded molecule or at least one triple-stranded molecule that comprises one or more complementary strand(s) or "complement(s)" of a particular sequence comprising a strand of the molecule.

Yeast Cells

Yeast strains that can be used in the compositions and methods described herein include, but are not limited to, *Saccharomyces cerevisiae, Saccharomyces uvae, Saccharomyces kluyveri, Schizosaccharomyces pombe, Kluyveromyces lactis, Hansenula polymorpha, Pichia pastoris, Pichia methanolica, Pichia kluyveri, Yarrowia lipolytica, Candida* sp., *Candida utilis, Candida* cacaoi, *Geotrichum* sp., and *Geotrichum* fermentans. Although much of the discussion herein relates to *Saccharomyces cerevisiae* which ectopically expresses an abnormally processed protein, this is merely for illustrative purposes. Other yeast strains can be substituted for *S. cerevisiae*.

Certain aspects of the disclosure relate to screening methods for identifying candidate therapeutic agents (e.g., pharmaceutical, chemical, or genetic agents). The methods described herein can optionally be carried out in yeast strains bearing mutations in the ERG6 gene, the PDR1 gene, the PDR3 gene, the PDR5 gene, the SNQ2 gene, and/or any other gene which affects membrane efflux pumps and/or increases permeability for drugs.

A nucleic acid encoding a TDP-43 protein may be transfected into a yeast cell using nucleic acid vectors that include, but are not limited to, plasmids, linear nucleic acid molecules, artificial chromosomes, and episomal vectors.

Three well known systems used for recombinant plasmid expression and replication in yeast cells include integrative plasmids, low-copy-number ARS-CEN plasmids, and high-copy-number 2μ plasmids. See Sikorski, "Extrachromosomal cloning vectors of *Saccharomyces cerevisiae*," in Plasmid, A Practical Approach, Ed. K. G. Hardy, IRL Press, 1993; and Yeast Cloning Vectors and Genes, Current Protocols in Molecular Biology, Section II, Unit 13.4, Eds., Ausubel et al., 1994.

An example of the integrative plasmids is YIp, which is maintained at one copy per haploid genome, and is inherited in Mendelian fashion. Such a plasmid, containing a gene of interest, a bacterial origin of replication and a selectable gene (typically an antibiotic-resistance marker), is produced in bacteria. The purified vector is linearized within the selectable gene and used to transform competent yeast cells.

An example of the low-copy-number ARS-CEN plasmids is YCp, which contains the autonomous replicating sequence (ARS1) and a centromeric sequence (CEN4). These plasmids are usually present at 1-2 copies per cell. Removal of the CEN sequence yields a YRp plasmid, which is typically present in 100-200 copies per cell. However, this plasmid is both mitotically and meiotically unstable.

An example of the high-copy-number 2μ plasmids is YEp, which contains a sequence approximately 1 kb in length (named the 2μ sequence). The 2μ sequence acts as a yeast replicon giving rise to higher plasmid copy number. However, these plasmids are unstable and require selection for maintenance. Copy number is increased by having on the plasmid a selection gene operatively linked to a crippled promoter.

A wide variety of plasmids can be used in the compositions and methods described herein. In one embodiment, the plasmid is an integrative plasmid (e.g., pRS303, pRS304, pRS305 or pRS306 or other integrative plasmids). In further embodiments, the plasmid is an episomal plasmid (e.g., p426GPD, p416GPD, p426TEF, p423GPD, p425GPD, p424GPD or p426GAL).

Regardless of the type of plasmid used, yeast cells are typically transformed by chemical methods (e.g., as described by Rose et al., 1990, Methods in Yeast Genetics, Cold Spring Harbor Laboratory Press, Cold Spring Harbor, N.Y.). The cells are typically treated with lithium acetate to achieve transformation efficiencies of approximately $10^4$ colony-forming units (transformed cells)/μg of DNA. Yeast perform homologous recombination such that the cut, selectable marker recombines with the mutated (usually a point mutation or a small deletion) host gene to restore function. Transformed cells are then isolated on selective media. Of course, any suitable means of introducing nucleic acids into yeast cells can be used.

The yeast vectors (plasmids) described herein typically contain a yeast origin of replication, an antibiotic resistance gene, a bacterial origin of replication (for propagation in bacterial cells), multiple cloning sites, and a yeast nutritional gene for maintenance in yeast cells. The nutritional gene (or "auxotrophic marker") is most often one of the following: 1) TRP1 (Phosphoribosylanthranilate isomerase); 2) URA3 (Orotidine-5'-phosphate decarboxylase); 3) LEU2 (3-Isopropylmalate dehydrogenase); 4) HIS3 (Imidazoleglycerol-phosphate dehydratase or IGP dehydratase); or 5) LYS2 (α-aminoadipate-semialdehyde dehydrogenase).

The yeast vectors (plasmids) described herein may also contain promoter sequences. A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively linked" and "operatively positioned" mean that a promoter is in a correct functional location and/or orientation in relation to a nucleic acid sequence to control transcriptional initiation and/or expression of that sequence.

A promoter may be one naturally associated with a nucleic acid sequence, as may be obtained by isolating the 5' non-coding sequences located upstream of the coding segment and/or exon. Such a promoter can be referred to as "endogenous." Alternatively, a promoter may be a recombinant or heterologous promoter, which refers to a promoter that is not normally associated with a nucleic acid sequence in its natural environment. Such promoters may include promoters of other genes and promoters not "naturally occurring." The promoters employed may be either constitutive or inducible.

For example, various yeast-specific promoters (elements) may be employed to regulate the expression of a RNA in yeast cells. Examples of inducible yeast promoters include GAL1-10, GAL1, GALL, GALS, TET, VP16 and VP16-ER. Examples of repressible yeast promoters include Met25. Examples of constitutive yeast promoters include glyceraldehyde 3-phosphate dehydrogenase promoter (GPD), alcohol dehydrogenase promoter (ADH), translation-elongation factor-1-alpha promoter (TEF), cytochrome c-oxidase promoter (CYC1), and MRP7. Autonomously replicating expression vectors of yeast containing promoters inducible by glucocorticoid hormones have also been described (Picard et al., 1990), including the glucocorticoid responsive element (GRE). These and other examples are described in Mumber et al., 1995; Ronicke et al., 1997; Gao, 2000, all incorporated herein by reference. Yet other yeast vectors containing constitutive or inducible promoters such as alpha factor, alcohol oxidase, and PGH may be used. For reviews, see Ausubel et al. and Grant et al., 1987.

Screening Assays

Certain aspects of the present disclosure provide methods of screening for a candidate drug (agent or compound) or a genetic factor that modulates TDP-43-induced toxicity or TDP-43-induced inclusion formation. Various types of candidate drugs may be screened by the methods described herein, including nucleic acids, polypeptides, small molecule compounds, and peptidomimetics. In some cases, genetic agents can be screened by contacting the yeast cell with a nucleic acid construct coding for a gene. For example, one may screen cDNA libraries expressing a variety of genes, to identify genes that modulate TDP-43-induced toxicity or TDP-43-induced inclusion formation.

For example, the identified drugs may modulate TDP-43-induced toxicity or TDP-43-induced inclusion formation. Accordingly, irrespective of the exact mechanism of action, drugs identified by the screening methods described herein are expected to provide therapeutic benefit to TDP-43 proteinopathies.

In certain embodiments, screening methods described herein use yeast cells that are engineered to express a TDP-43 protein. For chemical screens, suitable mutations of yeast strains designed to affect membrane efflux pumps and increase permeability for drugs can be used. For example, a yeast strain bearing mutations in the ERG6 gene, the PDR1 gene, the PDR3 gene, and/or the PDR5 gene is contemplated of use. For example, a yeast strain bearing mutations in membrane efflux pumps (erg6, pdr1, pdr3, and/or pdr5) has been successfully used in many screens to identify growth regulators (Jensen-Pergakes K L, et al., 1998. Antimicrob Agents Chemother 42:1160-7).

In certain embodiments, candidate drugs can be screened from large libraries of synthetic or natural compounds. One example is an FDA approved library of compounds that can be used by humans. In addition, compound libraries are commercially available from a number of companies including but not limited to Maybridge Chemical Co. (Trevillet, Cornwall, UK), Comgenex (Princeton, N.J.), Microsource (New Milford, Conn.), Aldrich (Milwaukee, Wis.), AKos Consulting and Solutions GmbH (Basel, Switzerland), Ambinter (Paris, France), Asinex (Moscow, Russia), Aurora (Graz, Austria), BioFocus DPI, Switzerland, Bionet (Camelford, UK), ChemBridge, (San Diego, Calif.), ChemDiv, (San Diego, Calif.), Chemical Block Lt, (Moscow, Russia), ChemStar (Moscow, Russia), Exclusive Chemistry, Ltd (Obninsk, Russia), Enamine (Kiev, Ukraine), Evotec (Hamburg, Germany), Indofine (Hillsborough, N.J.), Interbioscreen (Moscow, Russia), Interchim (Montlucon, France), Life Chemicals, Inc. (Orange, Conn.), Microchemistry Ltd. (Moscow, Russia), Otava, (Toronto, ON), PharmEx Ltd. (Moscow, Russia), Princeton Biomolecular (Monmouth Junction, N.J.), Scientific Exchange (Center Ossipee, N.H.), Specs (Delft, Netherlands), TimTec (Newark, Del.), Toronto Research Corp. (North York ON), UkrOrgSynthesis (Kiev, Ukraine), Vitas-M, (Moscow, Russia), Zelinsky Institute, (Moscow, Russia), and Bicoll (Shanghai, China). Combinatorial libraries are available and can be prepared. Libraries of natural compounds in the form of bacterial, fungal, plant and animal extracts are commercially available or can be readily prepared by methods well known in the art. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Several commercial libraries can be used in the screens.

Another embodiment relates to genetic screens. For example, genomic libraries and disruption libraries can be screened to find extragenic suppressors or enhancers of TDP-43-induced toxicity or TDP-43-induced inclusion formation. Because the yeast genome is small, 10,000 transformants of each type should be sufficient for good coverage.

One embodiment contemplates screening assays using fluorescent resonance energy transfer (FRET). FRET occurs when a donor fluorophore is in close proximity (10-60 A) to an acceptor fluorophore, and when the emission wavelength of the first overlaps the excitation wavelength of the second (Kenworthy A K et al., 2001. Methods. 24:289-96). FRET should occur when cyan fluorescent protein (CFP) and yellow fluorescent protein (YFP) fusion proteins are actually part of the same complex.

For example, a TDP-43 protein can be fused to CFP and to YFP respectively, and integrated in the yeast genome under the regulation of a GAL1-10 promoter. Cells are grown in galactose to induce expression. Upon induction, cells produce the fusion proteins, which aggregate and bring the CFP and YFP close together. Because proteins in the aggregates are tightly packed, the distance between the CFP and YFP is less than the critical value of 100 A that is necessary for FRET to occur. In this case, the energy released by the emission of CFP will excite the YFP, which in turn will emit at its characteristic wavelength. FRET based screening can be used to identify candidate compounds including, drugs, genes or other factors that can disrupt the interaction of CFP and YFP by maintaining the proteins in a state that does not allow aggregation to occur.

One embodiment contemplates screening assays using fluorescence activated cell sorting (FACS) analysis. FACS is a technique well known in the art, and provides the means of scanning individual cells for the presence of fluorescently labeled/tagged moiety. The method is unique in its ability to provide a rapid, reliable, quantitative, and multiparameter analysis on either living or fixed cells. For example, a TDP-43 protein can be suitably labeled, and provide a useful tool for the analysis and quantitation of protein aggregation as a result of other genetic or growth conditions of individual yeast cells as described above.

In particular embodiments, methods of the present disclosure relate to determining TDP-43-induced toxicity. One of the strongest aspects of yeast is the possibility of performing high throughput screens that may identify genes, peptides and other compounds with the potential to ameliorate toxicity. A large number of compounds can be screened under a variety of growth conditions and in a variety of genetic backgrounds. The toxicity screen has the advantage of not only selecting for compounds that interact with TDP-43, but also upstream or downstream targets that are not themselves cytotoxic and that are not yet identified.

For example, the Bioscreen-C system (Labsystem) permits the growth of up to 200 cell cultures at the same time, under different conditions. Growth rates are monitored optically, recorded automatically, and stored as digital files for further manipulations. Growth can be monitored in the presence of genetic libraries, chemicals, drugs, etc. to identify those that give a selective growth advantage or disadvantage. Mutants and chemicals from a variety of sources will be tested.

Certain embodiments provide methods of further testing those potential drugs that have been identified in the yeast system, in other model systems. The model systems include, but are not limited to, worms, flies, mammalian cells, and in vivo animal models.

Compounds

Compounds to be screened or identified using any of the methods described herein can include various chemical classes, though typically small organic molecules having a molecular weight in the range of 50 to 2,500 daltons. These compounds can comprise functional groups necessary for structural interaction with proteins (e.g., hydrogen bonding), and typically include at least an amine, carbonyl, hydroxyl, or carboxyl group, and preferably at least two of the functional chemical groups. These compounds often comprise cyclical carbon or heterocyclic structures and/or aromatic or polyaromatic structures (e.g., purine core) substituted with one or more of the above functional groups.

In alternative embodiments, compounds can also include biomolecules including, but not limited to, peptides, polypeptides, peptidomimetics (e.g., peptoids), amino acids, amino acid analogs, saccharides, fatty acids, steroids, purines, pyrimidines, derivatives or structural analogues thereof, polynucleotides, nucleic acid aptamers, and polynucleotide analogs.

Compounds can be identified from a number of potential sources, including: chemical libraries, natural product libraries, and combinatorial libraries comprised of random peptides, oligonucleotides, or organic molecules. Chemical libraries consist of diverse chemical structures, some of which are analogs of known compounds or analogs or compounds that have been identified as "hits" or "leads" in other drug discovery screens, while others are derived from natural products, and still others arise from non-directed synthetic organic chemistry. Natural product libraries re collections of microorganisms, animals, plants, or marine organisms which are used to create mixtures for screening by: (1) fermentation and extraction of broths from soil, plant or marine microorganisms, or (2) extraction of plants or marine organisms. Natural product libraries include polypeptides, non-ribosomal peptides, and variants (non-naturally occurring) thereof. For a review, see Science 282:63-68 (1998). Combinatorial libraries are composed or large numbers of peptides, oligonucleotides, or organic compounds as a mixture. These libraries are relatively easy to prepare by traditional automated synthesis methods, PCR, cloning, or proprietary synthetic methods. Of particular interest are non-peptide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers, Curr. Opin. Biotechnol. 8:701-707 (1997).

Identification of test compounds through the use of the various libraries herein permits subsequent modification of the test compound "hit" or "lead" to optimize the capacity of the "hit" or "lead" to prevent or suppress TDP-43-induced toxicity and/or TDP-43-induced inclusion formation.

The compounds identified above can be synthesized by any chemical or biological method. The compounds identified above can also be pure, or may be in a heterologous composition (e.g., a pharmaceutical composition), and can be prepared in an assay-, physiologic-, or pharmaceutically-acceptable diluent or carrier (see below).

Pharmaceutical Compositions

A compound that is found to prevent or suppress TDP-43-induced toxicity or the formation of TDP-43 aggregates (e.g., one that prevents or suppresses the formation, deposition, accumulation, or persistence of ubiquitinated, hyperphosphorylated forms of TDP-43 protein and/or C-terminal fragments thereof) in a cell can be formulated as a pharmaceutical composition, e.g., for administration to a subject to treat a TDP-43 proteinopathy such as frontotemporal lobar degeneration (FTLD), amyotrophic lateral sclerosis (ALS), certain types of motor neuron disease (MND), or any other TDP-43 proteinopathy.

A pharmaceutical composition typically includes a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. The composition can include a pharmaceutically acceptable salt, e.g., an acid addition salt or a base addition salt (see e.g., Berge et al., J. Pharm. Sci. 66:1-19, 1977).

The compound can be formulated according to standard methods. Pharmaceutical formulation is a well-established art, and is further described, e.g., in Gennaro (ed.), Remington: The Science and Practice of Pharmacy, 20th ed., Lippincott, Williams & Wilkins (2000) (ISBN: 0683306472); Ansel et al., Pharmaceutical Dosage Forms and Drug Delivery Systems, 7th Ed., Lippincott Williams & Wilkins Publishers (1999) (ISBN: 0683305727); and Kibbe (ed.), Handbook of Pharmaceutical Excipients American Pharmaceutical Association, 3rd ed. (2000) (ISBN: 091733096X).

In one embodiment, a compound that prevents or suppresses TDP-43-induced toxicity and/or TDP-43 aggregate formation in a cell can be formulated with excipient materials, such as sodium chloride, sodium dibasic phosphate heptahydrate, sodium monobasic phosphate, and a stabilizer. It can be provided, for example, in a buffered solution at a suitable concentration and can be stored at 2-8° C.

The pharmaceutical compositions may be in a variety of forms. These include, for example, liquid, semi-solid and solid dosage forms, such as liquid solutions (e.g., injectable and infusible solutions), dispersions or suspensions, tablets, capsules, pills, powders, liposomes and suppositories. The preferred form can depend on the intended mode of administration and therapeutic application. Typically compositions for the agents described herein are in the form of injectable or infusible solutions.

Such compositions can be administered by a parenteral mode (e.g., intravenous, subcutaneous, intraperitoneal, or intramuscular injection). The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, intracerebral, intracranial, intracarotid and intrasternal injection and infusion.

The composition can be formulated as a solution, microemulsion, dispersion, liposome, or other ordered structure suitable for stable storage at high concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating a compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of a compound plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, the compound can be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., Sustained and Controlled Release Drug Delivery Systems, J. R. Robinson, ed., Marcel Dekker, Inc., New York, 1978.

A compound identified as one that prevents or suppresses TDP-43-induced toxicity and/or TDP-43 aggregate formation in a cell can be modified, e.g., with a moiety that improves its stabilization and/or retention in circulation, e.g., in blood, serum, or other tissues, e.g., by at least 1.5, 2, 5, 10, or 50 fold. The modified compound can be evaluated to assess whether it can reach treatment sites of interest (e.g., locations of aggregate TDP-43) such as can occur in a cell in a subject with a TDP-43 proteinopathy such as ALS (e.g., by using a labeled form of the compound).

For example, the compound can be associated with a polymer, e.g., a substantially non-antigenic polymer, such as a polyalkylene oxide or a polyethylene oxide. Suitable polymers will vary substantially by weight. Polymers having molecular number average weights ranging from about 200 to about 35,000 Daltons (or about 1,000 to about 15,000, and 2,000 to about 12,500) can be used. For example, a compound can be conjugated to a water soluble polymer, e.g., a hydrophilic polyvinyl polymer, e.g., polyvinylalcohol or polyvinylpyrrolidone. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene (Pluronics); polymethacrylates; carbomers; and branched or unbranched polysaccharides.

When the compound is used in combination with a second agent (e.g., any additional therapies for a TDP-43 proteinopathy such as a decongestant or Rilutek®), the two agents can be formulated separately or together. For example, the respective pharmaceutical compositions can be mixed, e.g., just prior to administration, and administered together or can be administered separately, e.g., at the same or different times as elaborated below.

Methods for Treating a TDP-43 Proteinopathy

Disclosed herein are methods to treat or prevent a TDP-43 proteinopathy. In practicing the methods, effective amounts of the compounds or compositions described herein are administered. Such amounts are sufficient to achieve a therapeutically effective concentration of the compound or active component of the composition in vivo. The methods can be in vitro or in vivo methods.

A TDP-43 proteinopathy treated or whose symptoms are ameliorated by the compounds and compositions described is a disease associated with the formation, deposition, accumulation, or persistence of forms (e.g., ubiquitinated, hyperphosphorylated forms) of TDP-43 protein and/or C-terminal fragments thereof. (See, e.g., Cairns et al. (2007) The American Journal of Pathology 171(1):227). In certain embodiments, such diseases include, e.g., frontotemporal dementia (FTD) (e.g., frontotemporal lobar degeneration (FTLD)), amyotrophic lateral sclerosis (ALS), and certain types of motor neuron disease (MND). An FTLD can be, e.g.: (i) FTLD with tau-positive inclusions such as FTLD with Pick bodies, corticobasal degeneration (CBD), progressive supranuclear palsy (PSP0, or neurofibrillary tangle-only dementia; or (ii) FTLD with ubiquitin-positive, tau- and alpha-synuclein negative inclusions (UBI). (See, e.g., Kwong et al. (2007) Acta Neuropathol. 114:63-70). A TDP-43 proteinopathy can be a sporadic or familial (inherited) disorder (e.g., a sporadic or familial form of FTLD or ALS).

As used herein, a subject "suspected of having a TDP-43 proteinopathy" is one who exhibits one or more symptoms of a TDP-43 proteinopathy. Symptoms of a TDP-43 proteinopathy can include one or more of a variety of behavioral abnormalities such as, e.g., apathy or an unwillingness to talk; change in personality and mood (e.g., depression); lack of inhibition or lack of social tact; obsessive or repetitive behavior (e.g., compulsively shaving or collecting items); unusual verbal, physical, or sexual behavior; dramatic overeating; poor hygiene; and a general lack of awareness that any behavioral changes have occurred. Subjects affected by a TDP-43 proteinopathy can also manifest speech or memory abnormalities such as difficulty speaking (or finding a correct word), reading, and/or writing. Symptoms also include neurological abnormalities such as, e.g., twitching, cramping, muscle stiffness, muscle weakness, impaired balance, abnormal muscle postures, poor coordination, difficulty swallowing, and/or slurred speech. Any of the symptoms described above can range in severity, but generally increase in severity as a TDP-43 proteinopathy progresses.

A subject "at risk of developing" a TDP-43 proteinopathy is one with a family history of a TDP-43 proteinopathy and/or a genetic predisposition for developing a TDP-43 proteinopathy. For example, mutations in progranulin are associated with approximately 5-10% of all cases of FTD and mutations in superoxide dismutase 1 (SOD1) are associated with approximately 20% of familial ALS (see, e.g., Bruni et al. (2007) Neurology 69:140-147 and Battistini et al. (2005) J. Neurol. 252(7):782-8). Additional genetic mutations associated with familial and sporadic forms of ALS are described in Pasinelli et al. (2006) Nat. Rev. Neurosci. 7(9):710-23 and Gros-Louis et al. (2006) Biochim. Biophys. Acta. 1762(11-12):956-72. In some embodiments, a subject having a family history for developing a TDP-43 proteinopathy has one or more of the mutations identified as being associated with the particular proteinopathy (e.g., FTD or ALS). In other cases, a subject having a family history for developing a TDP-43 proteinopathy has only a medical record of the family history but has not been identified as having a particular genetic mutation associated with the proteinopathy (e.g., the individual has a family history of ALS but has a wild type SOD1 gene and/or lacks an SOD1 mutation that has been associated with ALS).

Methods for determining whether a subject has a TDP-43 proteinopathy include any of a number of qualitative and quantitative tests. For example, a medical practitioner (e.g., a doctor or nurse) can review the medical history of a subject and/or determine the number or type of symptoms that a particular subject presents. In some instances, a medical practitioner will perform one or more tests to rule out other conditions that have similar phenotypes. For example, a practitioner can perform any of an electromyography (EMG), a nerve conduction velocity (NCV) test, a magnetic resonance imaging (MRI) test, or a blood or urine test.

A compound useful for treating, preventing, or ameliorating one or more symptoms of a TDP-43 proteinopathy can be administered to a subject, e.g., a human subject, by a variety of methods. For many applications, the route of administration is one of: intravenous injection or infusion (IV), subcutaneous injection (SC), intraperitoneally (IP), or intramuscular injection. In some cases, administration can be directly into the CNS, e.g., intrathecal, intracerebroventricular (ICV), intracerebral, or intracranial. The compound can be administered as a fixed dose, or in a mg/kg dose. In other instances, administration can be oral (e.g., administered by inhalation), transdermal (topical), transmucosal, or rectal.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

The powders and tablets contain from 1% to 95% (w/w) of the active compound. In certain embodiments, the active compound ranges from 5% to 70% (w/w). Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

Where the compound is a polypeptide or otherwise particularly antigenic, the dose can also be chosen to reduce or avoid production of antibodies against the compound. The route and/or mode of administration of the agent can also be tailored for the individual case.

Dosage regimens are adjusted to provide the desired response, e.g., a therapeutic response or, when administered in combination with another agent, a combinatorial therapeutic effect. The dosage regimen can, for example, be capable of treating, preventing, or ameliorating one or more symptoms of a TDP-43 proteinopathy (or prevent or suppress the formation, deposition, accumulation, or persistence of ubiquitinated, phosphorylated (or hyperphosphorylated) forms of TDP-43 protein and/or C-terminal fragments thereof in one or more affected cells in a subject having a TDP-43 proteinopathy). The dose of a compound can be, optionally, formulated separately or together with an appropriate dose of a second therapeutic agent can be used to provide a subject with the agent. Suitable dosages and/or dose ranges for the compound include an amount sufficient to treat, prevent, or ameliorate one or more symptoms of a TDP-43 proteinopathy (or prevent or suppress the formation, deposition, accumulation, or persistence of ubiquitinated, hyperphosphorylated forms of TDP-43 protein and/or C-terminal fragments thereof in one or more affected cells in a subject having a TDP-43 proteinopathy). Such dosages can include, e.g., about 0.001 µg/kg to 10,000 µg/kg body weight of the subject, per dose. In another example, the dosage can be about 1 µg/kg to 100 µg/kg body weight of the subject, per dose. In another example, the dosage can be about 1 µg/kg to 30 µg/kg body weight of the subject, per dose, e.g., from 3 µg/kg to 10 µg/kg body weight of the subject, per dose.

A dose of a compound required to treat, prevent, or ameliorate one or more symptoms of a TDP-43 proteinopathy (or prevent or suppress the formation, deposition, accumulation, or persistence of ubiquitinated, hyperphosphorylated forms of TDP-43 protein and/or C-terminal fragments thereof in one or more affected cells in a subject having a TDP-43 proteinopathy) can depend on a variety of factors including, for example, the age, sex, and weight of a subject to be treated. Other factors affecting the dose administered to the subject include, e.g., the type or severity of the subject's TDP-43 proteinopathy. For example, a patient with advanced ALS can require a administration of a different dosage of a compound than a patient with a milder form of ALS. Other factors can include, e.g., other disorders concurrently or previously affecting the subject, the general health of the subject, the genetic disposition of the subject, diet, time of administration, rate of excretion, drug combination, and any other additional therapeutics that are administered to the subject. It should also be understood that a specific dosage and treatment regimen for any particular subject will depend upon the judgment of the treating medical practitioner. The amount of any active ingredients will also depend upon the particular described compound and the presence or absence and the nature of the additional therapeutic agents in a composition containing the compound.

Dosage unit form or "fixed dose" as used herein refers to physically discrete units suited as unitary dosages for the subjects to be treated; each unit contains a predetermined quantity of active compound calculated to produce the desired therapeutic effect (e.g., treating, preventing, or ameliorating one or more symptoms of a TDP-43 proteinopathy (or preventing or suppressing the formation, deposition, accumulation, or persistence of ubiquitinated, hyperphosphorylated forms of TDP-43 protein and/or C-terminal fragments thereof in one or more affected cells in a subject having a TDP-43 proteinopathy)) in association with the required pharmaceutical carrier and optionally in association with the other agent. Suitable administration frequencies are described elsewhere herein.

Following administration of one or more of the compounds described herein (or pharmaceutical compositions thereof) to a subject (e.g., a human patient), the efficacy of the treatment in ameliorating one or more symptoms of a TDP-43 proteinopathy can be assessed by comparing the number and/or severity of one or more symptoms presented by a patient before and after treatment. Alternatively, where administration of the compounds is used to prevent the occurrence of a TDP-43 proteinopathy, treatment efficacy can be assessed as a delay in presentation of, or a failure to present, one or more symptoms of a TDP-43 proteinopathy. The efficacy of a treatment (e.g., a compound or composition described herein) over time (e.g., a progressive improvement) in ameliorating one or more symptoms of a TDP-43 proteinopathy can be determined by assessing, e.g., the number or severity of one or more symptoms at multiple time points following treatment. For example, a subject (e.g., a patient) can have an initial assessment of the severity of his or her disorder (e.g., the number or severity of one or more symptoms of a TDP-43 proteinopathy), administered treatment, and then assessed subsequently to the treatment two or more times (e.g., at one week and one month; at one month at two months; at two weeks, one month, and six months; or six weeks, six months, and a year). Where one or more compounds or compositions are administered to a subject for a limited period of time (e.g., a predetermined duration) or number of administrations, the effect of treatment on ameliorating one or more symptoms of a TDP-43 proteinopathy can be assessed at various time points after the final treatment. For example, following the last administration of a dose of one or more compounds, the number or severity of a patient's symptoms can be assessed at 1 month (e.g., at 2 months, at 6 months, at one year, at two years, at 5 years or more) subsequent to the final treatment.

The efficacy of a treatment with one or more compounds (or compositions) described herein on one or more symptoms of a TDP-43 proteinopathy can be assessed as a monotherapy or as part of a multi-therapeutic regimen. For example, the compound(s) can be administered in conjunction with other clinically relevant treatments for TDP-43 proteinopathy including, but not limited to, physical or respiratory therapy, speech-language therapy, a decongestant, an anticonvulsant, and/or Rilutek®.

A compound or pharmaceutical composition thereof described herein can be administered to a subject as a combination therapy with another treatment (another active ingredients), e.g., a treatment for a TDP-43 proteinopathy such as ALS. For example, the combination therapy can include administering to the subject (e.g., a human patient) one or more additional agents that provide a therapeutic benefit to the subject who has, or is at risk of developing, (or suspected of having) a TDP-43 proteinopathy. Thus, the compound or pharmaceutical composition and the one or more additional agents are administered at the same time. Alternatively, the compound can be administered first in time and the one or more additional agents administered second in time. The one or more additional agents can be administered first in time and the compound administered second in time. The compound can replace or augment a previously or currently administered therapy. For example, upon treating with a compound of the invention, administration of the one or more additional agents can cease or diminish, e.g., be administered at lower levels. Administration of the previous therapy can also be maintained. In some instances, a previous therapy can be maintained until the level of the compound (e.g., the dosage or schedule) reaches a level sufficient to provide a therapeutic effect. The two therapies can be administered in combination.

It will be appreciated that in instances where a previous therapy is particularly toxic (e.g., a treatment for a TDP-43 proteinopathy that carries significant side-effects) or poorly tolerated by a subject (e.g., a patient), administration of the compound can be used to offset and/or lessen the amount of the previous therapy to a level sufficient to give the same or improved therapeutic benefit, but without the toxicity.

In some instances, when the subject is administered a compound or pharmaceutical composition of the invention, the first therapy is halted. The subject can be monitored for a first pre-selected result, e.g., an improvement in one or more symptoms of a TDP-43 proteinopathy such as any of those described herein (e.g., see above). In some cases, where the first pre-selected result is observed, treatment with the compound is decreased or halted. The subject can then be monitored for a second pre-selected result after treatment with the compound is halted, e.g., a worsening of a symptom of a TDP-43 proteinopathy. When the second pre-selected result is observed, administration of the compound to the subject can be reinstated or increased, or administration of the first therapy is reinstated, or the subject is administered both a compound and first therapy, or an increased amount of the compound and the first therapeutic regimen.

In addition, while the invention is not limited by any particular theory or mechanism of action, because the compounds identified herein can function at the molecular level to correct the TDP-43 proteinopathy, assessing the effect of a therapy on subject having a TDP-43 proteinopathy can be done by assessing, e.g., whether a decrease in, or prevention of, the formation, deposition, accumulation, or persistence of ubiquitinated, hyperphosphorylated forms of TDP-43 protein and/or C-terminal fragments thereof in one or more affected cells in a subject having (or suspected of having a TDP-43 proteinopathy) occurred.

When the terms "prevent," "preventing," or "prevention" are used herein in connection with a given treatment for a TDP-43 proteinopathy, they mean that the treated subject either does not develop a clinically observable level of the TDP-43 proteinopathy at all (e.g., the subject does not exhibit one or more symptoms of the TDP-43 proteinopathy or, at the molecular level, does not develop aggregate TDP-43 or the formation, deposition, accumulation, or persistence of ubiquitinated, hyperphosphorylated forms of TDP-43 protein and/or C-terminal fragments), or the condition develops more slowly and/or to a lesser degree (e.g., fewer symptoms or a lower amount of aggregate TDP-43) in the subject than it would have absent the treatment. These terms are not limited solely to a situation in which the subject experiences no aspect of the TDP-43 proteinopathy whatsoever. For example, a treatment will be said to have "prevented" the TDP-43 proteinopathy if it is given to a subject at risk of developing a TDP-43 proteinopathy and results in the subject's experiencing fewer and/or milder symptoms of the proteinopathy than otherwise expected. A treatment can "prevent" an TDP-43 proteinopathy (e.g., ALS) when the subject displays only mild overt symptoms of the TDP-43 proteinopathy. "Prevention" does not imply that there must have been no symptoms of a TDP-43 proteinopathy, or no aggregate TDP-43 or formation, deposition, accumulation, or persistence of ubiquitinated, hyperphosphorylated forms of TDP-43 protein and/or C-terminal fragments in any cell of a subject.

The following are examples of the practice of the invention. They are not to be construed as limiting the scope of the invention in any way.

EXAMPLES

Yeast Models of TDP-43 Aggregation and Toxicity

Several yeast strains were generated that enable constitutive or inducible expression of full-length human TDP-43. To facilitate the analysis of TDP-43 aggregation in vivo, GFP-tagged versions of human TDP-43 were also made. GFP-TDP-43 was expressed in yeast using a galactose-inducible promoter. Expression of GFP-tagged TDP-43 resulted in the formation of multiple cytoplasmic inclusions in yeast cells (FIG. 1). These findings demonstrate that yeast can be used as a model system for the formation of insoluble cytoplasmic TDP-43 aggregates.

Figure 2:
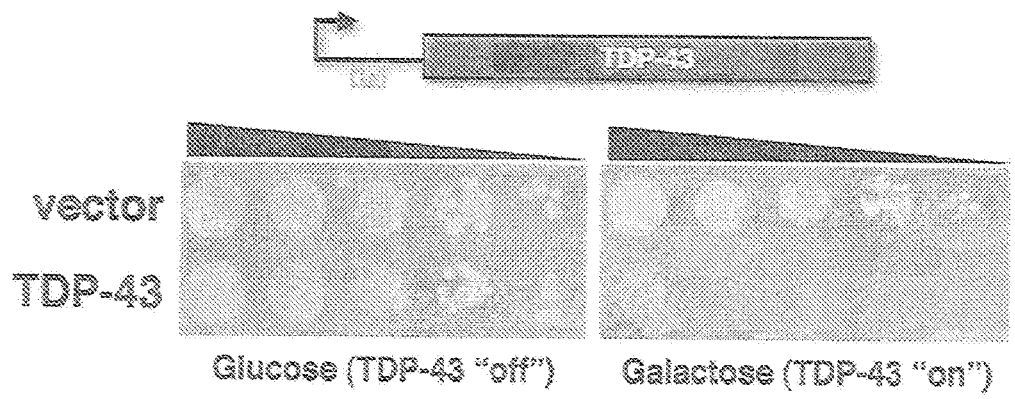
FIG. 2 is a photograph of yeast cells transformed with either an empty vector or a galactose-inducible TDP-43 expression plasmid. The cells were spotted on glucose or galactose and growth was assessed after two days. The transformants grew equally well on the control glucose plates (TDP-43 "off"), whereas TDP-43 expression profoundly inhibited growth (TDP-43 "on").

The effect of TDP-43 accumulation on cellular toxicity was also determined. Yeast cells were transformed with either an empty vector or a galactose-inducible TDP-43 expression plasmid. Serial dilutions of transformants were spotted on glucose or galactose and growth was assessed after two days. Expression of TDP-43 (in transformants grown on galactose plates) was found to be highly toxic to yeast cells (FIG. 2). These findings demonstrate that yeast can be used as a model system for TDP-43-induced cellular toxicity.

OTHER EMBODIMENTS

It is to be understood that, while the invention has been described in conjunction with the detailed description thereof, the foregoing description is intended to illustrate and not limit the scope of the invention. Other aspects, advantages, and modifications of the invention are within the scope of the claims set forth below.

---

What is claimed is:

1. A method of inducing toxicity in a yeast cell, the method comprising:
    providing a yeast cell comprising an expression construct comprising an inducible promoter operably linked to a nucleic acid encoding a polypeptide comprising a naturally occurring TAR DNA-binding protein 43 (TDP-43) protein, wherein the naturally occurring TDP-43 protein comprises an amino acid sequence that is at least 95% identical to amino acid residues 252-414 of SEQ ID NO:1, wherein expression of the nucleic acid and production of the polypeptide results in a decrease in growth or viability of the cell; and
    inducing a level of expression of the nucleic acid in the yeast cell that is toxic to the yeast cell.

2. A method of identifying a compound that prevents or suppresses TDP-43-induced toxicity, the method comprising:
    culturing a yeast cell in the presence of a candidate agent and under conditions that allow for expression of the nucleic acid at a level that, in the absence of the candidate agent, is sufficient to induce toxicity in the yeast cell, wherein the yeast cell comprises an expression construct comprising a promoter operably linked to a nucleic acid encoding a polypeptide comprising a naturally occurring TAR DNA-binding protein 43 (TDP-43) protein, wherein the naturally occurring TDP-43 protein comprises an amino acid sequence that is at least 95% identical to amino acid residues 252-414 of SEQ ID NO:1, wherein expression of the nucleic acid and production of the polypeptide results in a decrease in growth or viability of the cell;
    measuring cell growth or viability in the presence of the candidate agent; and
    comparing cell growth or viability measured in the presence of the candidate agent to cell growth or viability in the absence of the candidate agent,
    wherein if cell growth or viability is increased in the presence of the candidate agent as compared to in the absence of the candidate agent, then the candidate agent is identified as a compound that prevents or suppresses TDP-43-induced toxicity.

3. A method of identifying a compound that inhibits the formation or maintenance of cytoplasmic inclusions of TDP-43, the method comprising:
    providing a yeast cell comprising an expression construct comprising a nucleic acid encoding a polypeptide comprising a naturally occurring TDP-43 protein, wherein the naturally occurring TDP-43 protein comprises an amino acid sequence that is at least 95% identical to amino acid residues 252-414 of SEQ ID NO:1;
    culturing the yeast cell in the presence of a candidate agent and under conditions that allow for expression of the nucleic acid at a level that, in the absence of the candidate agent, is sufficient to result in the formation or maintenance of cytoplasmic inclusions of the protein;
    measuring the formation or maintenance of cytoplasmic inclusions of the protein in the presence of the candidate agent; and
    comparing the formation or maintenance of cytoplasmic inclusions of the protein measured in the presence of the candidate agent to the formation or maintenance of cytoplasmic inclusions of the protein in the absence of the candidate agent,
    wherein if formation or maintenance of cytoplasmic inclusions of the protein is decreased in the presence of the candidate agent as compared to in the absence of the candidate agent, then the candidate agent is identified as a compound that inhibits the formation or maintenance of cytoplasmic inclusions of TDP-43.

4. The method of claim 2, wherein expression of the nucleic acid and production of the polypeptide renders the cell non-viable.

5. The method of claim 2, wherein the expression construct is integrated in the genome of the yeast cell.

6. The method of claim 2, wherein the expression construct is an integrative plasmid.

7. The method of claim 6, wherein the integrative plasmid is pRS303, pRS304, pRS305, or pRS306.

8. The method of claim 2, wherein the promoter is an inducible promoter.

9. The method of claim 8, wherein the inducible promoter is GAL1-10, GAL1, GALL, GALS, GPD, ADH, TEF, CYC1, MRP7, MET25, TET, VP16, or VP16-ER.

10. The method of claim 2, wherein the promoter is a constitutively active promoter.

11. The method of claim 2, wherein the polypeptide comprises SEQ ID NO:1.

12. The method of claim 2, wherein the yeast is Saccharomyces cerevisiae, Saccharomyces uvae, Saccharomyces kluyveri, Schizosaccharomyces pombe, Kluyveromyces lactis, Hansenula polymorpha, Pichia pastoris, Pichia metha-

*nolica, Pichia kluyveri, Yarrowia lipolytica, Candida* sp., *Candida utilis, Candida cacaoi, Geotrichum* sp., or *Geotrichum fermentans*.

13. The method of claim 2, wherein the polypeptide is a fusion protein comprising a detectable protein.

14. The method of claim 13, wherein the detectable protein is a fluorescent protein, an enzyme, or an epitope.

15. The method of claim 13, wherein the detectable protein is a fluorescent protein selected from the group consisting of a red fluorescent protein, green fluorescent protein, blue fluorescent protein, yellow fluorescent protein, and cyan fluorescent protein.

16. The method of claim 2, wherein at least one gene that encodes a protein involved in drug efflux or cell permeability is disrupted.

17. The method of claim 16, wherein the at least one gene is PDR1, PDR3, PDR5, SNQ2, or ERG6.

18. The method of claim 1, wherein the inducible promoter is GAL1-10, GAL1, GALL, GALS, GPD, ADH, TEF, CYC1, MRP7, MET25, TET, VP16, or VP16-ER.

19. The method of claim 1, wherein the naturally occurring TDP-43 protein is at least 95% identical to SEQ ID NO:1.

20. The method of claim 2, wherein the naturally occurring TDP-43 protein is at least 95% identical to SEQ ID NO:1.

21. The method of claim 3, wherein the naturally occurring TDP-43 protein is at least 95% identical to SEQ ID NO:1.

22. The method of claim 1, wherein the polypeptide comprises SEQ ID NO:1.

23. The method of claim 3, wherein the polypeptide comprises SEQ ID NO:1.

24. The method of claim 1, wherein the polypeptide comprises amino acid residues 252-414 of SEQ ID NO:1.

25. The method of claim 2, wherein the polypeptide comprises amino acid residues 252-414 of SEQ ID NO:1.

26. The method of claim 3, wherein the polypeptide comprises amino acid residues 252-414 of SEQ ID NO:1.

* * * * *

SEQUENCE LISTING

```
<160> NUMBER OF SEQ ID NOS: 2

<210> SEQ ID NO 1
<211> LENGTH: 414
<212> TYPE: PRT
<213> ORGANISM: Homo sapiens

<400> SEQUENCE: 1

Met Ser Glu Tyr Ile Arg Val Thr Glu Asp Glu Asn Asp Glu Pro Ile
1               5                   10                  15

Glu Ile Pro Ser Glu Asp Asp Gly Thr Val Leu Leu Ser Thr Val Thr
                20                  25                  30

Ala Gln Phe Pro Gly Ala Cys Gly Leu Arg Tyr Arg Asn Pro Val Ser
            35                  40                  45

Gln Cys Met Arg Gly Val Arg Leu Val Glu Gly Ile Leu His Ala Pro
        50                  55                  60

Asp Ala Gly Trp Gly Asn Leu Val Tyr Val Val Asn Tyr Pro Lys Asp
65                  70                  75                  80

Asn Lys Arg Lys Met Asp Glu Thr Asp Ala Ser Ser Ala Val Lys Val
                85                  90                  95

Lys Arg Ala Val Gln Lys Thr Ser Asp Leu Ile Val Leu Gly Leu Pro
                100                 105                 110

Trp Lys Thr Thr Glu Gln Asp Leu Lys Glu Tyr Phe Ser Thr Phe Gly
            115                 120                 125

Glu Val Leu Met Val Gln Val Lys Lys Asp Leu Lys Thr Gly His Ser
        130                 135                 140

Lys Gly Phe Gly Phe Val Arg Phe Thr Glu Tyr Glu Thr Gln Val Lys
145                 150                 155                 160

Val Met Ser Gln Arg His Met Ile Asp Gly Arg Trp Cys Asp Cys Lys
                165                 170                 175

Leu Pro Asn Ser Lys Gln Ser Gln Asp Glu Pro Leu Arg Ser Arg Lys
            180                 185                 190

Val Phe Val Gly Arg Cys Thr Glu Asp Met Thr Glu Asp Glu Leu Arg
        195                 200                 205

Glu Phe Phe Ser Gln Tyr Gly Asp Val Met Asp Val Phe Ile Pro Lys
    210                 215                 220

Pro Phe Arg Ala Phe Ala Phe Val Thr Phe Ala Asp Asp Gln Ile Ala
225                 230                 235                 240

Gln Ser Leu Cys Gly Glu Asp Leu Ile Ile Lys Gly Ile Ser Val His
                245                 250                 255
```

```
Ile Ser Asn Ala Glu Pro Lys His Asn Ser Asn Arg Gln Leu Glu Arg
                260                 265                 270
Ser Gly Arg Phe Gly Gly Asn Pro Gly Gly Phe Gly Asn Gln Gly Gly
            275                 280                 285
Phe Gly Asn Ser Arg Gly Gly Ala Gly Leu Gly Asn Asn Gln Gly
        290                 295                 300
Ser Asn Met Gly Gly Gly Met Asn Phe Gly Ala Phe Ser Ile Asn Pro
305                 310                 315                 320
Ala Met Met Ala Ala Gln Ala Ala Leu Gln Ser Ser Trp Gly Met
                325                 330                 335
Met Gly Met Leu Ala Ser Gln Gln Asn Gln Ser Gly Pro Ser Gly Asn
            340                 345                 350
Asn Gln Asn Gln Gly Asn Met Gln Arg Glu Pro Asn Gln Ala Phe Gly
        355                 360                 365
Ser Gly Asn Asn Ser Tyr Ser Gly Ser Asn Ser Gly Ala Ala Ile Gly
        370                 375                 380
Trp Gly Ser Ala Ser Asn Ala Gly Ser Gly Ser Gly Phe Asn Gly Gly
385                 390                 395                 400
Phe Gly Ser Ser Met Asp Ser Lys Ser Ser Gly Trp Gly Met
                405                 410

<210> SEQ ID NO 2
<211> LENGTH: 4236
<212> TYPE: DNA
<213> ORGANISM: Homo sapiens

<400> SEQUENCE: 2
ggtgggcggg gggaggaggc ggccctagcg ccatttgtg ggagcgaagc ggtggctggg     60
ctgcgcttgg gtccgtcgct gcttcggtgt ccctgtcggg cttcccagca gcggcctagc    120
gggaaaagta aaagatgtct gaatatattc gggtaaccga agatgagaac gatgagccca    180
ttgaaatacc atcggaagac gatgggacgg tgctgctctc cacggttaca gcccagtttc    240
caggggcgtg tgggcttcgc tacaggaatc cagtgtctca gtgtatgaga ggtgtccggc    300
tggtagaagg aattctgcat gccccagatg ctggctgggg aaatctggtg tatgttgtca    360
actatccaaa agataacaaa agaaaaatgg atgagacaga tgcttcatca gcagtgaaag    420
tgaaaagagc agtccagaaa catccgatt taatagtgtt gggtctccca tggaaaacaa    480
ccgaacagga cctgaaagag tattttagta cctttggaga agttcttatg gtgcaggtca    540
agaaagatct taagactggt cattcaaagg ggtttggctt tgttcgtttt acggaatatg    600
aaacacaagt gaaagtaatg tcacagcgac atatgataga tggacgatgg tgtgactgca    660
aacttcctaa ttctaagcaa agccaagatg agcctttgag aagcagaaaa gtgtttgtgg    720
ggcgctgtac agaggacatg actgaggatg agctgcggga gttcttctct cagtacgggg    780
atgtgatgga tgtcttcatc cccaagccat tcagggcctt tgcctttgtt acatttgcag    840
atgatcagat tgcgcagtct cttgtggag aggacttgat cattaaagga atcagcgttc    900
atatatccaa tgccgaacct aagcacaata gcaatagaca gttagaaaga agtggaagat    960
ttggtggtaa tccaggtggc tttgggaatc agggtggatt tggtaatagc agaggggtg   1020 gagctggttt ggggaacaat caaggtagta atatgggtgg tgggatgaac tttggtgcgt   1080
tcagcattaa tccagccatg atggctgccg cccaggcagc actacagagc agttgggta   1140 tgatgggcat gttagccagc cagcagaacc agtcaggccc atcgggtaat aaccaaaacc   1200
aaggcaacat gcagagggag ccaaaccagg ccttcggttc tggaaataac tcttatagtg   1260
```

```
gctctaattc tggtgcagca attggttggg gatcagcatc caatgcaggg tcgggcagtg      1320
gttttaatgg aggctttggc tcaagcatgg attctaagtc ttctggctgg ggaatgtaga      1380
cagtggggtt gtggttggtt ggtatagaat ggtgggaatt caaattttc taaactcatg       1440 gtaagtatat tgtaaaatac atatgtacta agaattttca aaattggttt gttcagtgtg     1500
gagtatattc agcagtattt ttgacatttt tctttagaaa aaggaagagc taaaggaatt      1560
ttataagttt tgttacatga aaggttgaaa tattgagtgg ttgaaagtga actgctgttt      1620
gcctgattgg taaaccaaca cactacaatt gatatcaaaa ggtttctcct gtaatatttt      1680
atccctggac ttgtcaagtg aattctttgc atgttcaaaa cggaaaccat tgattagaac      1740
tacattcttt acccccttgtt ttaatttgaa ccccaccata tggattttttt tccttaagaa     1800 aatctccttt taggagatca tggtgtcaca gtgtttggtt cttttgtttt gttttttaac      1860
acttgtctcc cctcatacac aaaagtacaa tatgaagcct tcatttaatc tctgcagttc      1920
atctcatttc aaatgtttat ggaagaagca cttcattgaa agtagtgctg taaatattct      1980
gccataggaa tactgtctac atgctttctc attcaagaat tcgtcatcac gcatcacagg      2040 ccgcgtctt tgacggtgggt gtcccatttt tatccgctac tctttatttc atggagtcgt      2100
atcaacgcta tgaacgcaag gctgtgatat ggaaccagaa ggctgtctga acttttgaaa      2160
ccttgtgtgg gattgatggt ggtgccgagg catgaaaggc tagtatgagc gagaaaagga     2220
gagagcgcgt gcagagactt ggtggtgcat aatggatatt ttttaacttg gcgagatgtg     2280
tctctcaatc ctgtggcttt ggtgagagag tgtgcagaga gcaatgatag caaataatgt     2340
acgaatgttt tttgcattca aaggacatcc acatctgttg gaagactttt aagtgagttt      2400
ttgttcttag ataacccaca ttagatgaat gtgttaagtg aaatgatact tgtactcccc     2460 ctacccctt gtcaactgct gtgaatgctg tatggtgtgt gttctcttct gttactgata      2520
tgtaagtgtg gcaatgtgaa ctgaagctga tgggctgaga acatggactg agcttgtggt      2580
gtgctttgca ggaggacttg aagcagagtt caccagtgag ctcaggtgtc tcaaagaagg     2640
gtggaagttc taatgtctgt tagctaccca taagaatgct gttttgctgca gttctgtgtc     2700 ctgtgcttgg atgcttttta taagagttgt cattgttgga aattcttaaa taaaactgat     2760
ttaaataata tgtgtctttg ttttgcagcc ctgaatgcaa agaattcata gcagttaatt     2820
cccctttttt gacccttttg agatggaact ttcataaagt ttcttggcag tagtttattt     2880
tgcttcaaat aaacttattt gaaaagttgt ctcaagtcaa atggattcat cacctgtcat     2940
gcattgacac ctgatacccaa gacttaattg gtatttgttc ttgcattggc caaagtgaaa    3000 atttttttt ttcttttgaa atctagtttt gaataagtct gggtgaccgc acctaaaatg    3060
gtaagcagta ccctccggct ttttcttagt gcctctgtgc atttgggtga tgttctattt     3120
acatggcctg tgtaaatctc cattgggaag tcatgccttc taaaaagatt cttatttggg    3180
ggagtgggca aaatgttgat tattttctaa tgctttgtag caaagcatat caattgaaaa    3240
gggaatatca gcaccttcct agtttgggat ttgaaaagtg gaattaattg cagtagggat    3300
aaagtagaag aaaccacaaa ttatcttgtg cctgaaatcc attaagaggc ctgatagctt    3360
taagaattag ggtgggttgt ctgtctggaa gtgttaagtg aatgggctt tgtcctccag     3420 gaggtggggg aatgtggtaa cattgaatac agttgaataa aatcgcttac aaaactcaca    3480
ctctcacaat gcattgttaa gtatgtaaaa gcaataacat tgattctctg ttgtactttt    3540
ttgtaactaa ttctgtgaga gttgagctca ttttctagtt ggaagaatgt gatatttgtt    3600
gtgttggtag tttacctaat gcccttacct aattagatta tgataaatag gtttgtcatt    3660
```

-continued

```
ttgcaagtta cataaacatt tatcaatgaa gtcatccttt agacttgtaa tcgccacatt    3720
gtttcattat tcagtttcct ctgtaaaggg atcttgagtt gttttaattt ttttttttctg   3780 catctgaatc tgcatgattt ccaaaccctg taccatctga attttgcatt ttagcacttg    3840
cactattact cagcagcagt aacatggtaa cacttaaaat ggtactcggg gacctccaaa    3900
gactaaactg acaagccttc aaggagccca ggggtaagtt aacttgtcaa cggcatggtt    3960
taatcccttc tttacacttg tgtaaatttc agttactggt catagaaggc tttcaatgtt    4020
gagtggcctt ttattaacat gtttatggta ctgcatagat acgggtattt attttaccct    4080
aagaagattt tgaagtttaa aagtacttaa actatttggc aaagatttgt ttttaaaaat    4140
ctatttggtc aatctaaatg cattcattct aaaaaatttt ttgaaccaga taaataaaat    4200 tttttttttga caccacaaaa aaaaaaaaaa aaaaaa                             4236
```